(12) United States Patent
Filippo

(10) Patent No.: US 12,321,043 B2
(45) Date of Patent: Jun. 3, 2025

(54) SOFT CONTACT LENS AND A PACKAGING COMPRISING SUCH A SOFT CONTACT LENS

(71) Applicant: Cataltheia Group, Inc., Wilmington, DE (US)

(72) Inventor: Alessandro Filippo, Puntarenas (CR)

(73) Assignee: Cataltheia Group, Inc.

( * ) Notice: Subject to any disclaimer, the term of this patent is extended or adjusted under 35 U.S.C. 154(b) by 568 days.

(21) Appl. No.: 17/776,780

(22) PCT Filed: Nov. 16, 2020

(86) PCT No.: PCT/IB2020/060741
§ 371 (c)(1),
(2) Date: May 13, 2022

(87) PCT Pub. No.: WO2021/099909
PCT Pub. Date: May 27, 2021

(65) Prior Publication Data
US 2022/0390762 A1      Dec. 8, 2022

(30) Foreign Application Priority Data
Nov. 21, 2019   (IT) .................. 102019000021849

(51) Int. Cl.
*G02C 7/04* (2006.01)
*G02B 1/04* (2006.01)

(52) U.S. Cl.
CPC .............. *G02C 7/04* (2013.01); *G02B 1/043* (2013.01)

(58) Field of Classification Search
CPC ...... G02C 7/04; G02C 2202/24; G02B 1/043; A61P 27/02; A45C 11/005; B29D 11/00067
(Continued)

(56) References Cited

U.S. PATENT DOCUMENTS 8,784,867 B2 *   7/2014   Samuel ............... A61K 9/0051
                                                              585/351
2006/0073184 A1   4/2006   Xia et al.
(Continued)

FOREIGN PATENT DOCUMENTS

CN    108853116 A    11/2018
CN    109828384 A    5/2019
(Continued)

OTHER PUBLICATIONS

Peng, C. C., Kim, J., & Chauhan, A. (2010). Extended delivery of hydrophilic drugs from silicone-hydrogel contact lenses containing vitamin E diffusion barriers. Biomaterials, 31(14), 4032-4047. https://doi.org/10.1016/j.biomaterials.2010.01.113.
(Continued)

*Primary Examiner* — William R Alexander
(74) *Attorney, Agent, or Firm* — Volpe Koenig

(57) ABSTRACT

A soft contact lens (4) comprises a solid component, which is based on a polymer, and a liquid component which is distributed in the solid component and which comprises at least one compound which is selected from vitamin E, vitamin B2 and the respective derivatives thereof. The contact lens has a degree of transmission of type A ultraviolet radiation greater than 50% and a degree of transmission of type B ultraviolet radiation greater than 20%.

19 Claims, 1 Drawing Sheet

(58) Field of Classification Search
USPC .................................................. 351/159.02
See application file for complete search history.

(56) References Cited

U.S. PATENT DOCUMENTS

| | | | |
|---|---|---|---|
| 2013/0178518 A1* | 7/2013 | Samuel | A61K 31/355 514/458 |
| 2017/0351115 A1 | 12/2017 | Filippo | |
| 2020/0054555 A1 | 2/2020 | Rout et al. | |

FOREIGN PATENT DOCUMENTS

| | | |
|---|---|---|
| CN | 107260655 B | 3/2021 |
| EP | 2103552 A1 | 3/2009 |
| JP | 2005502392 A | 1/2005 |
| JP | 2005084558 A | 3/2005 |
| JP | 2006039529 A | 2/2006 |
| JP | 2013500302 A | 1/2013 |
| JP | 2015-507649 A | 3/2015 |
| JP | 2015509205 A | 3/2015 |
| JP | 2015230398 A | 12/2015 |
| JP | 2019504168 A | 2/2019 |
| JP | 2019509516 A | 4/2019 |
| KR | 100741610 B1 | 7/2007 |
| WO | 2006085351 A1 | 8/2006 |
| WO | 2009154169 A1 | 12/2009 |
| WO | 2013086077 A1 | 6/2013 |
| WO | 2015186723 A1 | 12/2015 |
| WO | 2017090128 A1 | 6/2017 |
| WO | 2017131588 A1 | 8/2017 |
| WO | 2018172511 A1 | 9/2018 |

OTHER PUBLICATIONS

Decision of Refusal for corresponding Japanese Application No. 2022-529625 dated Dec. 24, 2024, 5 pages long.

* cited by examiner

SOFT CONTACT LENS AND A PACKAGING COMPRISING SUCH A SOFT CONTACT LENS

TECHNICAL FIELD

The present invention relates to a soft contact lens having the features set out in the preamble of the main claim.

In particular, the present invention relates to a soft contact lens which is capable of slowing down myopia progression.

The invention is further directed towards a packaging comprising such a soft contact lens.

TECHNOLOGICAL BACKGROUND

Myopia is a very common sight defect and as a result of which parallel light rays from outside the eye are not focused correctly on the retina, but instead in front of it.

This sight defect is often a result of a not perfectly spherical shape of the eyeball, in particular of a shape elongated along its optical axis.

The onset of myopia generally occurs from childhood and increases with growth. Therefore, there is noted a progressive increase in the degree of the myopia which tends to increase up to a maximum value which depends from person to person.

An instrument which is widely used to correct sight defects and in particular ametropias, such as myopia, is constituted by contact lenses and, among them, soft contact lenses.

One of the characteristics which make the soft contact lenses particularly appreciated by users with respect to other types of contact lenses (rigid or semi-rigid) is certainly the greater comfort thereof during use once being worn.

This advantageous characteristic is given by the high hydrophilic capacities of the lens which, by containing a relevant percentage of water, allows a greater level of compatibility between the lens and the eye, in addition to a greater degree of deformability of the lens which allows it to adapt better to the surface of the eye.

Soft contact lenses are conventionally produced by means of a process which provides for a first step of obtaining a semifinished dry product which is lens-shaped and made from polymer material and which, in turn, can be obtained by polymerization of a monomer directly from a mould (moulding technique) or by means of turning a disc of already polymerized material (turning technique).

Independently of the technique used for the preparation thereof, the semi-finished dry product is subsequently hydrated by means of immersion in a saline solution, which is optionally buffered, and which is formed by approximately 1% by weight of sodium chloride in water (known as physiological solution). The polymer material used is typically provided with optimum hydrophilic properties, for example, a polymer admixture based on HEMA or based on silicone, so that a relevant quantity of saline solution between 25% and 75% is absorbed in the semi-finished dry product.

The absorption of the liquid component, in addition to conferring on the lens the above-mentioned characteristics of compatibility and softness, also involves a physical expansion of the semi-finished dry product, both radial and linear, thereby bringing about both the final dimensions of the contact lens and the optical properties thereof.

The contact lens so obtained thereby comprises a solid component which defines the structural portion of the lens and which is constituted by the polymer material, and a liquid component which is constituted by the saline solution and which is distributed substantially uniformly in the solid component.

Among contact lenses, there are known and widespread lenses which are capable of protecting the eye of the user from the action of cell degradation of the tissues caused by ultraviolet radiation (UV rays).

In fact, it is known that the action of UV rays can lead to damage, including severe damage, to some tissues, such as, for example, the lens (causing, for example, important pathologies such as cataracts) or the cornea or the retina (damage which is potentially even more dangerous because some types of retina cells are not capable of regeneration).

In order to achieve this advantageous effect, there are introduced into the contact lenses, generally during the production process thereof, compounds which are capable of absorbing ultraviolet rays.

These compounds, which are generally known by the expression "UV filters" or "anti-UV" or by the term "UV blockers", generally belong to the family of the benzophenones or the family of benzotriazoles.

In accordance with the blocking action applied by the anti-UV compounds, the contact lenses can be classified as class 1 contact lenses or as class 2 contact lenses.

Class 1 contact lenses must be able to absorb at least 90% of ultraviolet radiation of the type A (UVA, defined as electromagnetic radiation having a wavelength between 400 and 315 nm) and 99% of ultraviolet radiation of type B (UVB, defined as electromagnetic radiation having a wavelength between 315 and 280 nm) while the class 2 contact lenses must be able to absorb at least 70% of UVA radiation and 95% of UVB radiation.

The degree of transmission of the ultraviolet radiation of the contact lenses is measured in accordance with the standard ANSI Z80.20 provided by the American National Standards Institute (ANSI).

DISCLOSURE OF THE INVENTION

The problem addressed by the present invention is to provide a soft contact lens which is realized in such a manner that the use thereof over time assists in slowing down the myopia progression of a user.

This problem is solved by the present invention by means of a soft contact lens constructed according to the appended claims.

In a first aspect thereof, therefore, the present invention is directed towards a soft contact lens comprising a solid component, which is based on a polymer and a liquid component which is distributed in the solid component.

The contact lens preferably has a degree of transmission of type A ultraviolet radiation greater than 50% and a degree of transmission of type B ultraviolet radiation greater than 20%.

The liquid component preferably comprises at least one compound which is selected from vitamin E, vitamin B2 and the derivatives thereof.

As a result of these characteristics, the contact lens according to the invention allows myopia progression of a user to be delayed, therefore preventing damage to the ocular tissues by the ultraviolet radiation.

This advantageous effect is obtained by allowing the passage through the contact lens of a large portion of ultraviolet radiation both of the type A and of the type B, and, at the same time, releasing in the eye, in a slow and gradual manner, a suitable quantity of vitamin E and/or vitamin B2.

The ultraviolet radiation, which comes typically from solar radiation and, passing through the contact lens, comes into contact with the tissues of the eye, also carries out an action of delaying the myopia progression.

In fact, the ultraviolet radiation acts, on the one hand, by activating the gene EGR1, a suppressor of myopia, and, on the other hand, by stimulating the production of dopamine inside the eye.

Dopamine is a catecholamine, the molecular structure of which is illustrated in formula (I) illustrated below.

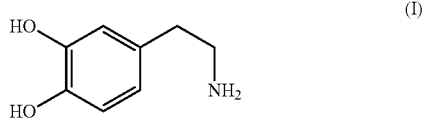 [SMILES: NCCc1ccc(O)c(O)c1]

Dopamine is a neurotransmitter and, within the eye, is involved in the mediation of different functions, including the development of the retinal tissue, the transmission of the visual signal and the development of the correct refraction. Furthermore, dopamine has a relevant influence on the control of the growth of the eyeball. In particular, it has been observed that the action thereof slows down the axial growth of the eyeball, thereby slowing down the potential elongation thereof along the optical axis, which is a primary cause of myopia.

As a result of this particular action, it is considered that the presence of an adequate concentration of dopamine in the eye is capable of effectively delaying myopia progression. In fact, it has been shown how the myopia progression can be delayed by a high level of activity in the open air.

In order to obtain a contact lens having the characteristics of transmissibility of ultraviolet radiation set out above, it is simply necessary to drastically limit or more preferably to completely prevent the addition of anti-UV compounds to the composition of the contact lens.

The possible negative consequences of the exposure of the eye to the ultraviolet radiation are further adequately counteracted by the release in the eye of vitamin E and/or vitamin B2 which is present in the contact lens.

In fact, these compounds effectively combat the oxidative action of the UV rays which can lead to the degradation of the tissues. Vitamin E is a liposoluble antioxidant and is important in preventing the phenomena of oxidation because it blocks the action of the free radicals. There exist 8 types of vitamin E, tocotrienols and tocopherols. Among these, the vitamin compound which is most active and powerful is α-tocopherol.

Vitamin B2 (riboflavin) carries out an action of reinforcing the tissues as a result of an action of natural cross-linking resulting from the individual interaction with the UV radiation of the sunlight. In particular, the collagen fibres which form the cornea by means of covalent bonds between fibrils of the stroma are reinforced.

As a result of the characteristics set out above, therefore, the contact lens according to the present invention can advantageously be used not only for correcting myopia but also for preventing or at least limiting the deterioration of this sight defect.

In a second aspect thereof, the present invention is directed towards a packaging comprising a soft contact lens which is constructed according to the first aspect described above and which is immersed in a preservation solution which comprises at least one compound which is selected from vitamin E, vitamin B2 and the derivatives thereof at a concentration which is at least equal to the one present in the liquid component of the contact lens.

In at least one of the above-mentioned aspects, the present invention may further have one or more of the following preferred features.

In a first embodiment, the contact lens comprises both vitamin B2 (or a derivative thereof) and vitamin E (or a derivative thereof).

In this manner, the positive effects of both substances are synergistically combined in order to increase the resistance of the eye to the degrading action of ultraviolet radiation.

The solid component of the soft contact lens is provided to confer shape and structure on the contact lens and is preferably constructed from hydrophilic polymer, such as, for example, HEMA or silicone.

However, the soft contact lens of the present invention may be constructed by using any other polymer or copolymer which is suitable for this purpose and which is normally used in this field.

The liquid component of the soft contact lens is capable of promoting the compatibility between the lens and the eye of a user of the contact lens.

The liquid component is preferably distributed inside the solid component in a substantially uniform manner.

The liquid component is an aqueous solution and preferably a saline solution with a suitable concentration of NaCl, for example, of approximately 0.9 g/l.

The liquid component preferably has an osmolarity between 150 and 350 mOsm, preferably between 280 and 310 mOsm.

In a preferred embodiment, the liquid component also comprises a suitable quantity of lubricating compounds. Examples of suitable lubricating compounds comprise polyvinyl alcohols, polysaccharides, such as, for example, trehalose, the derivatives of cellulose, such as, for example, hydroxypropyl cellulose, methyl cellulose and carboxymethyl cellulose, and polyethers, such as, for example, polyethylene glycols. Such compounds may be present in the liquid compound at concentrations between approximately 0.1% and approximately 5% (on the basis of weight).

In an embodiment, the liquid component further comprises compounds which regulate the rheological properties which are capable of conferring on the liquid component characteristics of visco-elasticity which are as similar as possible to those of lacrimal fluid.

In an embodiment, the compounds which regulate the rheological properties comprise hyaluronic acid or a derivative thereof, preferably a salt thereof, or a polysaccharide, preferably galactoxyloglucan extracted from tamarind seeds (TSP) having a suitable molecular weight, for example, between 500 KDalton and 1000 KDalton.

The presence of such compounds which regulate the rheological properties, as a result of the high molecular weight thereof, allows the vitamin E and/or vitamin B2 (or the respective derivatives thereof) to be retained inside the contact lens for a longer time in such a manner that they are released in the eye in a slower and more gradual manner.

This also allows the use of the contact lenses according to the invention for longer replacement times to be provided for, for example, weekly or monthly times.

In an embodiment, the contact lens has a degree of transmission of type A ultraviolet radiation greater than 70% and a degree of transmission of type B ultraviolet radiation greater than 50%. More preferably, the contact lens has a degree of transmission of type A and type B ultraviolet radiation greater than 90%, in an even more preferable manner greater than 99%.

In an embodiment, the vitamin E is α-tocopherol.

In a greatly preferred embodiment, the vitamin E is α-tocopherol which is functionalized with polyethylene glycol succinate (TPGS).

As a result of the structure thereof, vitamin E-TPGS has the capacity to penetrate deeply into the tissues, which allows it to carry out more effectively the individual anti-oxidative action thereof and further also to facilitate the solubilization of other compounds, in particular vitamin B2 by increasing the absorption and the bioavailability thereof through the different corneal layers as far as the retinal tissue.

Preferably, the concentration (on the basis of weight) of vitamin E or the derivative thereof is at least 0.00001%, more preferably between 0.0001% and 2%, even more preferably it is between 0.01% and 1.5%, and in an even more preferable manner it is between 0.1% and 1%.

In a particularly preferred manner, the vitamin E is an α-tocopherol which is functionalized with polyethylene glycol succinate and is present at a concentration (on the basis of weight) between 0.1% and 1%, preferably approximately 0.5%. Preferably, the concentration (on the basis of weight) of vitamin B2 or the derivative thereof is at least 0.001%, more preferably it is between 0.001% and 0.2%, even more preferably it is between 0.01% and 0.1%.

In a particularly preferred manner, the vitamin B2 (riboflavin) is present at a concentration (on the basis of weight) of approximately 0.075%.

BRIEF DESCRIPTION OF THE DRAWINGS

The features of the invention will be better appreciated from the following detailed description of a preferred embodiment thereof which is illustrated by way of non-limiting example with reference to the appended drawings, in which.

PREFERRED EMBODIMENT OF THE INVENTION

In the appended Figures, a soft contact lens constructed according to the present invention is generally designated 4.

The soft contact lens 4 is preferably a corrective lens but generally it may be of any known type.

The soft contact lens 4 is constructed according to the following process.

In a first step, there is constructed, according to techniques which are generally conventional per se (by moulding or turning), a semi-finished dry product of polymer material which is capable of conferring on the lens the final structure and formation. The semi-finished dry product can be obtained from a polymer admixture based on HEMA or from any other polymer or copolymer which is suitable for this purpose and which is normally used in the field, for example, a silicone-based polymer.

In a subsequent processing step, the semi-finished dry product is hydrated by immersion in an aqueous solution which is advantageously agitated so that there is absorbed in the solid component in a substantially uniform manner a liquid component which promotes the comfortable use of the contact lens and therefore the compatibility thereof with the eye of a user.

At the end of the hydration step, the soft contact lens 4 is therefore ready to be packaged and subsequently sterilized by means of processing in an autoclave at approximately 120° C. for a time of approximately 20 minutes.

Figure 1:
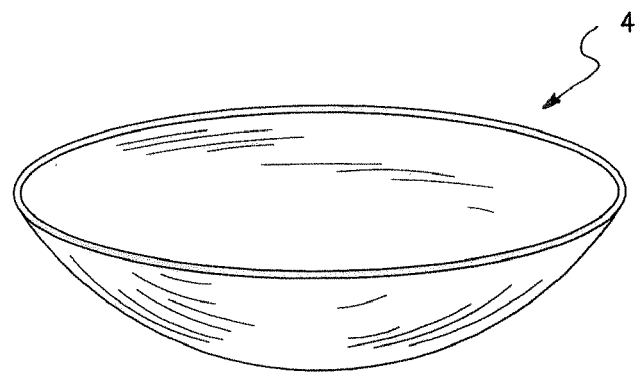
FIG. 1 is a schematic, perspective view of a contact lens which is constructed according to the present invention.
Figure 2:
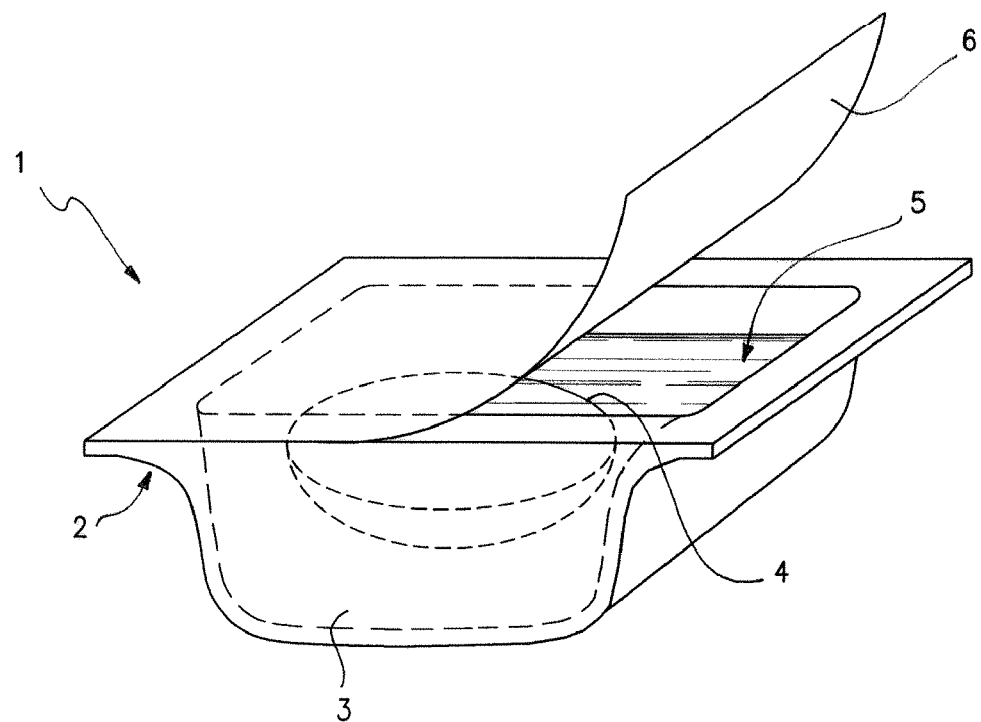
FIG. 2 is a schematic, perspective view of a packaging for the storage and preservation of the contact lens of FIG. 1.

FIG. 2 illustrates a packaging for storing and preserving the soft contact lens 4 which is generally designated 1. The packaging 1 comprises a support 2 which is constructed, for example, from plastics material and which is formed so as to define a container 3, inside which the soft contact lens 4 is immersed in a preservation solution 5.

The packaging 1 further comprises a membrane 6 which is connected, for example, by means of thermal welding, to a peripheral edge of the support 2 so as to seal the container 3 and to prevent the discharge of the soft contact lens 4 or the preservation solution 5.

For greater clarity, FIG. 2 illustrates the membrane 6 in a partially raised position.

According to a first aspect of the invention, the aqueous solution in which the semi-finished dry product is immersed for the hydration processing comprises vitamin E, vitamin B2 and the respective derivatives thereof.

In particular, in the preferred example described herein, the aqueous solution comprises in addition to sodium chloride at a concentration of approximately 0.9 g/l:

0.5% of α-tocopherol which is functionalized with polyethylene glycol succinate (vitamin E-TPGS) and
0.075 of riboflavin (vitamin B2).

The aqueous solution does not have any benzophenones, benzotriazoles or other anti-UV compounds so that the contact lens 4 has a degree of transmission of UVA and UVB radiation greater than 90%.

Optionally, the aqueous solution may comprise lubricating compounds, such as, for example, polyvinyl alcohols, or compounds which regulate the rheological properties, such as, for example, sodium hyaluronate or galactoxyloglucan which is extracted from tamarind seeds at a concentration of approximately 0.2%.

In addition, the aqueous solution may comprise a surfactant agent, a disinfecting agent, for example, disodium EDTA, at quantities of approximately 0.1%, a buffering agent, such as, for example, sodium phosphate, so as to preserve an overall pH value of approximately from 7.3 to 7.4.

The soft contact lens 4 obtained in this manner therefore comprises, in the same manner as a conventional lens, a solid component which is substantially constituted by the polymer material and a liquid component which is distributed in a substantially uniform manner in the solid component, in which the liquid component has substantially the same composition as the aqueous solution in which the semi-finished dry product has been immersed.

The liquid component portion present in the soft contact lens is between 25% and 75%.

According to another aspect of the invention, the preservation solution 5 comprises a concentration of vitamin E, vitamin B2 or the respective derivatives thereof at least equal to the concentration present in the liquid component of the soft contact lens 4.

The soft contact lens 4, once it has been extracted from the packaging 1 and put in place by the user, as it does not contain any compound capable of absorbing the UV rays, allows a virtually total passage of the ultraviolet radiation which can therefore effectively carry out the action of delaying the myopia progression, by acting on the EGR1 gene and particularly stimulating the production of dopamine inside the eye.

At the same time, the soft contact lens 4 slowly and gradually releases in the eye of the user vitamin E and/or vitamin B2 (or the respective derivatives thereof) which prevent the damaging effects of exposure to the useful sunlight.

The contact lenses according to the invention can be produced so as to have to be replaced at a monthly frequency or at a greater frequency, for example, on a daily basis, weekly basis or fortnightly basis, in accordance with the preselected polymer material and the characteristics thereof for preserving the liquid component.

Preferably, the contact lens is of the type for weekly or daily replacement.

Therefore, the present invention solves the problem set out above by providing a soft contact lens which is capable of preventing or at least limiting the progression of myopia.

Furthermore, at the same time it affords a number of other advantages, including the fact of allowing the construction of this soft contact lens by means of a simple and inexpensive production process.

The invention claimed is:

1. A soft contact lens (4) comprising:
   a solid component, which is based on a polymer, and which is provided to confer shape and structure on the soft contact lens, and
   a liquid component which is distributed in the solid component, wherein:
   the soft contact lens has a degree of transmission of type A ultraviolet radiation greater than 90%,
   the soft contact lens has a degree of transmission of type B ultraviolet radiation greater than 90%, and
   the liquid component comprises at least one compound which is selected from the group consisting of: vitamin E, vitamin B2, and respective derivatives thereof.

2. The soft contact lens according to claim 1, wherein the vitamin E is α-tocopherol.

3. The soft contact lens according to claim 1, wherein the vitamin E is an α-tocopherol which is functionalized with polyethylene glycol succinate (TPGS).

4. The soft contact lens according to claim 1, wherein the concentration of the vitamin E or a derivative thereof in the liquid component is between 0.0001% and 2%.

5. The soft contact lens according to claim 1, wherein the concentration of the vitamin B2 or a derivative thereof in the liquid component is between 0.001% and 0.2%.

6. The soft contact lens according to claim 1, wherein the liquid component comprises a quantity of compounds which regulate the rheological properties and which are selected from the group consisting of: hyaluronic acid, derivatives thereof and a polysaccharide.

7. The soft contact lens according to claim 6, wherein the polysaccharide is galactoxyloglucan extracted from tamarind seeds (TSP).

8. The soft contact lens according to claim 1, wherein the concentration of the vitamin E or a derivative thereof in the liquid component is between 0.01% and 1.5%.

9. The soft contact lens according to claim 1, wherein the concentration of the vitamin E or a derivative thereof in the liquid component is between 0.1% and 1%.

10. The soft contact lens according to claim 1, wherein the concentration of the vitamin B2 or a derivative thereof in the liquid component is between 0.01% and 0.1%.

11. A packaging (1) comprising:
   a soft contact lens (4) which is immersed in a preservation solution (5), the soft contact lens comprising:
     a solid component, which is based on a polymer, and which is provided to confer shape and structure on the soft contact lens; and
     a liquid component which is distributed in the solid component, the liquid component comprises at least one compound which is selected from the group consisting of: vitamin E, vitamin B2, and respective derivatives thereof;
   wherein the soft contact lens has a degree of transmission of type A ultraviolet radiation greater than 50%, and the soft contact lens has a degree of transmission of type B ultraviolet radiation greater than 20%; and
   wherein the preservation solution (5) comprises at least one compound of the group at a concentration which is at least equal to the one present in the liquid component of the soft contact lens.

12. The packaging according to claim 11, wherein the soft contact lens has a degree of transmission of type A ultraviolet radiation greater than 70% and a degree of transmission of type B ultraviolet radiation greater than 50%.

13. The packaging according to claim 12, wherein the soft contact lens has a degree of transmission of type A and type B ultraviolet radiation greater than 90%.

14. The packaging according to claim 11, wherein the vitamin E is α-tocopherol.

15. The packaging according to claim 11, wherein the vitamin E is an α-tocopherol which is functionalized with polyethylene glycol succinate (TPGS).

16. The packaging according to claim 11, wherein the concentration of the vitamin E or a derivative thereof in the liquid component is between 0.0001% and 2%.

17. The packaging according to claim 11, wherein the concentration of the vitamin B2 or a derivative thereof in the liquid component is between 0.001% and 0.2%.

18. The packaging according to claim 11, wherein the liquid component comprises a quantity of compounds which regulate the rheological properties and which are selected from the group consisting of: hyaluronic acid, derivatives thereof and a polysaccharide.

19. The packaging according to claim 18, wherein the polysaccharide is galactoxyloglucan extracted from tamarind seeds (TSP).

* * * * *